(12) United States Patent
Cabiri (10) Patent No.: US 8,152,779 B2
(45) Date of Patent: Apr. 10, 2012

(54) NEEDLE ASSEMBLY FOR DRUG PUMP

(75) Inventor: Oz Cabiri, Macabim (IL)

(73) Assignee: Medimop Medical Projects Ltd., Ra'anana (IL)

( * ) Notice: Subject to any disclaimer, the term of this patent is extended or adjusted under 35 U.S.C. 154(b) by 609 days.

(21) Appl. No.: 12/345,818

(22) Filed: Dec. 30, 2008

(65) Prior Publication Data

US 2010/0168683 A1 Jul. 1, 2010

(51) Int. Cl.
*A61M 5/31* (2006.01)
*A61M 5/20* (2006.01)
(52) U.S. Cl. .......... 604/240; 604/137
(58) Field of Classification Search .......... 604/137, 604/240, 165.01, 165.04, 110
See application file for complete search history.

(56) References Cited

U.S. PATENT DOCUMENTS

| | | | |
|---|---|---|---|
| 1,795,630 A | 3/1931 | Wilson | |
| 3,212,685 A | 10/1965 | Swan et al. | |
| 4,195,636 A | 4/1980 | Behnke | |
| 4,300,554 A | 11/1981 | Hessberg et al. | |
| 4,403,987 A | 9/1983 | Gottinger | |
| 4,435,173 A | 3/1984 | Siposs et al. | |
| 4,599,082 A | 7/1986 | Grimard | |
| 4,867,743 A | 9/1989 | Vaillancourt | |
| 4,886,499 A | 12/1989 | Cirelli et al. | |
| 5,109,850 A | 5/1992 | Blanco et al. | |
| 5,190,521 A | 3/1993 | Hubbard et al. | |
| 5,383,865 A | 1/1995 | Michel | |
| 5,478,315 A | 12/1995 | Brothers et al. | |
| 5,505,709 A | 4/1996 | Funderburk et al. | |
| 5,593,390 A | 1/1997 | Castellano et al. | |
| 5,616,132 A | 4/1997 | Newman | |
| 5,643,218 A | 7/1997 | Lynn et al. | |
| 5,662,678 A | 9/1997 | Macklin | |
| 5,690,618 A | 11/1997 | Smith et al. | |
| 5,766,186 A | 6/1998 | Faraz et al. | |
| 5,800,420 A | 9/1998 | Gross et al. | |
| 5,807,375 A | 9/1998 | Gross et al. | |

(Continued)

FOREIGN PATENT DOCUMENTS

WO 9407553 A1 4/1994

(Continued)

OTHER PUBLICATIONS

International Preliminary Report on Patentability and Written Opinion issued Jul. 5, 2011 in International Application No. PCT/US2009/069552.

(Continued)

*Primary Examiner* — Kevin C Sirmons
*Assistant Examiner* — Bradley Osinski
(74) *Attorney, Agent, or Firm* — Panitch Schwarze Belisario & Nadel LLP (57) ABSTRACT

A needle assembly adapted for fluid communication with a vial containing a substance to be delivered to a subject, the needle assembly including a needle held in a needle holder, the needle holder confined to move in a housing, and an activation mechanism for activating delivery of the substance through the needle, the activation mechanism including a safety latch that initially impedes movement of the needle holder, wherein when the safety latch is placed on the subject, the safety latch moves to a position that permits moving the needle holder to cause the needle to protrude outwards of the housing to pierce the subject to allow administration of the substance to the subject.

12 Claims, 6 Drawing Sheets

U.S. PATENT DOCUMENTS

| | | | |
|---|---|---|---|
| 5,814,020 A * | 9/1998 | Gross | 604/141 |
| 5,851,197 A | 12/1998 | Marano et al. | |
| 5,858,001 A | 1/1999 | Tsals et al. | |
| 5,931,814 A | 8/1999 | Alex et al. | |
| 5,954,697 A | 9/1999 | Srisathapat et al. | |
| 5,957,895 A | 9/1999 | Sage et al. | |
| 5,968,011 A | 10/1999 | Larsen et al. | |
| 6,074,369 A | 6/2000 | Sage et al. | |
| 6,186,982 B1 | 2/2001 | Gross et al. | |
| 6,200,289 B1 | 3/2001 | Hochman et al. | |
| 6,200,296 B1 | 3/2001 | Dibiasi et al. | |
| 6,277,098 B1 | 8/2001 | Klitmose et al. | |
| 6,277,099 B1 | 8/2001 | Strowe et al. | |
| 6,287,283 B1 | 9/2001 | Ljunggreen et al. | |
| 6,391,005 B1 | 5/2002 | Lum et al. | |
| 6,485,461 B1 | 11/2002 | Mason et al. | |
| 6,500,150 B1 | 12/2002 | Gross et al. | |
| 6,503,231 B1 | 1/2003 | Prausnitz et al. | |
| 6,517,517 B1 | 2/2003 | Farrugia et al. | |
| 6,558,351 B1 | 5/2003 | Steil et al. | |
| 6,589,229 B1 | 7/2003 | Connelly et al. | |
| 6,595,956 B1 | 7/2003 | Gross et al. | |
| 6,645,181 B1 | 11/2003 | Lavi et al. | |
| 6,652,482 B2 | 11/2003 | Hochman | |
| 6,656,158 B2 | 12/2003 | Mahoney et al. | |
| 6,656,159 B2 | 12/2003 | Flaherty | |
| 6,699,218 B2 | 3/2004 | Flaherty et al. | |
| 6,743,211 B1 | 6/2004 | Prausnitz et al. | |
| 6,749,587 B2 | 6/2004 | Flaherty | |
| 6,768,425 B2 | 7/2004 | Flaherty et al. | |
| 6,786,890 B2 | 9/2004 | Preuthun et al. | |
| 6,805,687 B2 | 10/2004 | Dextradeur et al. | |
| 6,824,529 B2 | 11/2004 | Gross et al. | |
| 6,843,782 B2 | 1/2005 | Gross et al. | |
| 6,854,620 B2 | 2/2005 | Ramey | |
| 6,905,298 B1 | 6/2005 | Haring | |
| 6,960,192 B1 | 11/2005 | Flaherty et al. | |
| 7,001,360 B2 | 2/2006 | Veasey et al. | |
| 7,060,054 B2 | 6/2006 | Nissels | |
| 7,060,059 B2 | 6/2006 | Keith et al. | |
| 7,128,727 B2 | 10/2006 | Flaherty et al. | |
| 7,144,384 B2 | 12/2006 | Gorman et al. | |
| 7,247,149 B2 | 7/2007 | Beyerlein | |
| 7,250,037 B2 | 7/2007 | Shermer et al. | |
| 7,291,159 B2 | 11/2007 | Schmelzeisen-Redeker et al. | |
| 7,303,549 B2 | 12/2007 | Flaherty et al. | |
| 7,390,314 B2 | 6/2008 | Stutz, Jr. et al. | |
| 7,407,493 B2 | 8/2008 | Cane' | |
| 7,455,663 B2 | 11/2008 | Bikovsky | |
| 7,530,964 B2 | 5/2009 | Lavi et al. | |
| 7,565,208 B2 | 7/2009 | Harris et al. | |
| 7,569,050 B2 | 8/2009 | Moberg et al. | |
| 7,585,287 B2 | 9/2009 | Bresina et al. | |
| 7,588,559 B2 | 9/2009 | Aravena et al. | |
| 7,628,770 B2 | 12/2009 | Ethelfeld | |
| 7,637,891 B2 | 12/2009 | Wall | |
| 7,641,649 B2 | 1/2010 | Moberg et al. | |
| 7,678,079 B2 | 3/2010 | Shermer et al. | |
| 7,686,787 B2 | 3/2010 | Moberg et al. | |
| 7,699,829 B2 | 4/2010 | Harris et al. | |
| 7,713,238 B2 | 5/2010 | Mernoe | |
| 7,744,589 B2 | 6/2010 | Mounce et al. | |
| 7,749,194 B2 | 7/2010 | Edwards et al. | |
| 7,806,868 B2 | 10/2010 | De Polo et al. | |
| 2001/0025168 A1 | 9/2001 | Gross et al. | |
| 2001/0041869 A1 | 11/2001 | Causey et al. | |
| 2002/0010423 A1 | 1/2002 | Gross et al. | |
| 2002/0040208 A1 | 4/2002 | Flaherty et al. | |
| 2002/0055711 A1 | 5/2002 | Lavi et al. | |
| 2002/0123740 A1 | 9/2002 | Flaherty et al. | |
| 2002/0169215 A1 | 11/2002 | Meng | |
| 2003/0009133 A1 | 1/2003 | Ramey | |
| 2003/0135159 A1 | 7/2003 | Daily et al. | |
| 2003/0171717 A1 | 9/2003 | Farrugia et al. | |
| 2004/0010207 A1 | 1/2004 | Flaherty et al. | |
| 2004/0092873 A1 | 5/2004 | Moberg | |
| 2004/0127857 A1 | 7/2004 | Shemesh et al. | |
| 2004/0186419 A1 | 9/2004 | Cho | |
| 2004/0260233 A1 | 12/2004 | Garibotto et al. | |
| 2005/0033234 A1 | 2/2005 | Sadowski et al. | |
| 2005/0065466 A1 | 3/2005 | Vedrine | |
| 2005/0065472 A1 | 3/2005 | Cindrich et al. | |
| 2005/0171512 A1 | 8/2005 | Flaherty | |
| 2005/0197650 A1 | 9/2005 | Sugimoto et al. | |
| 2005/0203461 A1 | 9/2005 | Flaherty et al. | |
| 2005/0238507 A1 | 10/2005 | Dilanni et al. | |
| 2005/0283114 A1 | 12/2005 | Bresina et al. | |
| 2006/0095014 A1 | 5/2006 | Ethelfeld | |
| 2006/0122577 A1 | 6/2006 | Poulsen et al. | |
| 2006/0173406 A1 | 8/2006 | Hayes et al. | |
| 2006/0173439 A1 | 8/2006 | Thorne et al. | |
| 2006/0229569 A1 | 10/2006 | Lavi et al. | |
| 2006/0264889 A1 | 11/2006 | Moberg et al. | |
| 2006/0264890 A1 | 11/2006 | Moberg et al. | |
| 2006/0264894 A1 | 11/2006 | Moberg et al. | |
| 2006/0283465 A1 | 12/2006 | Nickel et al. | |
| 2006/0293722 A1 | 12/2006 | Slatkine et al. | |
| 2007/0021733 A1 | 1/2007 | Hansen et al. | |
| 2007/0049865 A1 | 3/2007 | Radmer et al. | |
| 2007/0073228 A1 | 3/2007 | Mernoe et al. | |
| 2007/0118405 A1 | 5/2007 | Campbell et al. | |
| 2007/0167912 A1 | 7/2007 | Causey et al. | |
| 2007/0185449 A1 | 8/2007 | Mernoe | |
| 2007/0203454 A1 | 8/2007 | Shermer et al. | |
| 2008/0033367 A1 | 2/2008 | Haury et al. | |
| 2008/0033369 A1 | 2/2008 | Kohlbrenner et al. | |
| 2008/0051711 A1 | 2/2008 | Mounce et al. | |
| 2008/0051730 A1 | 2/2008 | Bikovsky | |
| 2008/0059133 A1 | 3/2008 | Edwards et al. | |
| 2008/0097381 A1 | 4/2008 | Moberg et al. | |
| 2008/0108951 A1 | 5/2008 | Jerde et al. | |
| 2008/0140006 A1 | 6/2008 | Eskuri et al. | |
| 2008/0140018 A1 | 6/2008 | Enggaard et al. | |
| 2008/0188813 A1 | 8/2008 | Miller et al. | |
| 2008/0215006 A1 | 9/2008 | Thorkild | |
| 2008/0269723 A1 | 10/2008 | Mastrototaro et al. | |
| 2008/0294143 A1 | 11/2008 | Tanaka et al. | |
| 2008/0306449 A1 | 12/2008 | Kristensen et al. | |
| 2008/0312601 A1 | 12/2008 | Cane | |
| 2008/0319416 A1 | 12/2008 | Yodfat et al. | |
| 2009/0054750 A1 | 2/2009 | Jennewine | |
| 2009/0069784 A1 | 3/2009 | Estes et al. | |
| 2009/0088731 A1 | 4/2009 | Campbell et al. | |
| 2009/0093792 A1 | 4/2009 | Gross et al. | |
| 2009/0093793 A1 | 4/2009 | Gross et al. | |
| 2009/0124977 A1 | 5/2009 | Jensen | |
| 2009/0143735 A1 | 6/2009 | De Polo et al. | |
| 2009/0149830 A1 | 6/2009 | Spector | |
| 2009/0182277 A1 | 7/2009 | Carter | |
| 2009/0234319 A1 | 9/2009 | Marksteiner | |
| 2009/0240240 A1 | 9/2009 | Hines et al. | |
| 2009/0253973 A1 | 10/2009 | Bashan et al. | |
| 2009/0259176 A1 | 10/2009 | Yairi | |
| 2009/0326509 A1 | 12/2009 | Muse et al. | |
| 2010/0030198 A1 | 2/2010 | Beebe et al. | |
| 2010/0057057 A1 | 3/2010 | Hayter et al. | |
| 2010/0076412 A1 | 3/2010 | Rush et al. | |
| 2010/0094255 A1 | 4/2010 | Nycz et al. | |
| 2010/0100076 A1 | 4/2010 | Rush et al. | |
| 2010/0100077 A1 | 4/2010 | Rush et al. | |
| 2010/0106098 A1 | 4/2010 | Atterbury et al. | |
| 2010/0121314 A1 | 5/2010 | Iobbi | |
| 2010/0145303 A1 | 6/2010 | Yodfat et al. | |
| 2010/0162548 A1 | 7/2010 | Leidig | |
| 2010/0204657 A1 | 8/2010 | Yodfat et al. | |
| 2010/0234830 A1 | 9/2010 | Straessler et al. | |
| 2010/0274112 A1 | 10/2010 | Hoss et al. | |
| 2010/0274192 A1 | 10/2010 | Mernoe | |
| 2010/0280499 A1 | 11/2010 | Yodfat et al. | |

FOREIGN PATENT DOCUMENTS

| | | |
|---|---|---|
| WO | WO02/02165 | 1/2002 |
| WO | 2006037434 A1 | 4/2006 |
| WO | 2006069380 A1 | 6/2006 |
| WO | 2007051563 A1 | 5/2007 |
| WO | 2009044401 | 4/2009 |

OTHER PUBLICATIONS

Office Action issued Jul. 13, 2011 in U.S. Appl. No. 12/559,563.
Daikyo Crystal Zenitha polymer, Manufactured by Daikyo Seiko, Ltd.
Copaxonea, Manufactured by Teva Pharmaceutical Industries Ltd.
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312; Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.
Office Action issued Sep. 30, 2010 in U.S. Appl. No. 12/689,250.
Int'l Search Report issued Jan. 12, 2011 in Int'l Application No. PCT/US2010/048556; Written Opinion.
U.S. Appl. No. 60/997,459, filed Oct. 2, 2007.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
Int'l Preliminary Report on Patentability issued Sep. 1, 2011 in Int'l Application No. PCT/US2010/048556.

* cited by examiner

NEEDLE ASSEMBLY FOR DRUG PUMP

FIELD OF THE INVENTION

The present invention generally relates to external drug pumps, and particularly to a needle assembly for a drug pump with safety features.

BACKGROUND OF THE INVENTION

External drug pumps are typically used to deliver to patients substances which contain large molecules which cannot be digested when administered orally, such as insulin. Typically, the pump is adhered to the abdomen of the patient and delivers the substance to the patient via a cannula that is inserted into the patient's skin.

SUMMARY OF THE INVENTION

The present invention seeks to provide an improved needle assembly for a drug pump with safety features, as is described more in detail hereinbelow.

There is thus provided in accordance with an embodiment of the present invention a needle assembly adapted for fluid communication with a vial containing a substance to be delivered to a subject, the needle assembly including a needle held in a needle holder, the needle holder confined to move in a housing, and an activation mechanism for activating delivery of the substance through the needle, the activation mechanism including a safety latch that initially impedes movement of the needle holder, wherein when the safety latch is placed on the subject, the safety latch moves to a position that permits moving the needle holder to cause the needle to protrude outwards of the housing to pierce the subject to allow administration of the substance to the subject.

In accordance with an embodiment of the present invention the safety latch is pivotally mounted on a base about a pivot. The safety latch may be arranged to selectively pivot in and out of a complimentary shaped groove formed in the base.

In accordance with an embodiment of the present invention the safety latch includes a first arrestor at a distal end thereof and a second arrestor proximal to and spaced from the first arrestor, the first and second arrestors being arranged for selectively arresting motion of the needle holder.

In accordance with an embodiment of the present invention the safety latch initially impedes movement of the needle holder by being in a position wherein the first arrestor abuts against an ear that projects from a bottom portion of the needle holder, thereby arresting movement of the needle holder.

In accordance with an embodiment of the present invention when the safety latch is placed on the subject, the safety latch moves to a position such that the first arrestor moves away from the ear of the needle holder to permit movement of the needle holder.

In accordance with an embodiment of the present invention a control button is provided that has a shaft. A slanted tongue protrudes from a periphery of the shaft at a lower end thereof. When the safety latch is placed on the subject and the control button is moved, the slanted tongue applies a force against a ramp formed on the needle holder, thereby causing the needle holder to move and to rotate as the needle moves outwards of the housing. The needle holder can rotate sufficiently so that the ear is arrested by the second arrestor. Moving the safety latch off the subject causes the second arrestor to move away from the ear and causes the needle holder to continue to rotate due to the slanted tongue still applying a force on the ramp. The needle holder rotates until the slanted tongue moves off the ramp, whereupon the needle holder moves so that the ear gets caught on a shoulder formed on the housing, thereby trapping the needle in the housing.

In accordance with an embodiment of the present invention when the control button is moved so that the slanted tongue applies the force against the ramp, the control button becomes locked in the housing.

BRIEF DESCRIPTION OF THE DRAWINGS

The present invention will be understood and appreciated more fully from the following detailed description taken in conjunction with the drawings in which:

FIGS. 3-9 are simplified illustrations of operation of an activation mechanism of the apparatus of FIGS. 1-2, constructed and operative in accordance with an embodiment of the present invention, wherein:

DETAILED DESCRIPTION OF EMBODIMENTS

Figure 1:
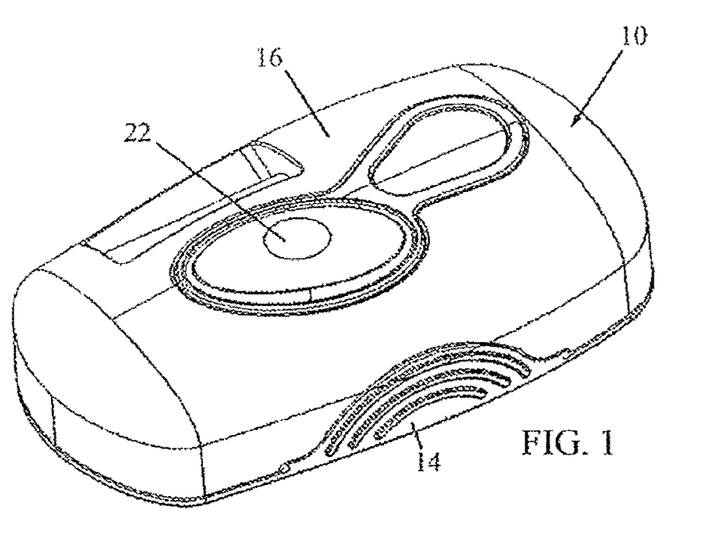
FIGS. 1 and 2 are simplified illustrations of apparatus for administering a substance to a subject, in accordance with an embodiment of the present invention.
Figure 2:
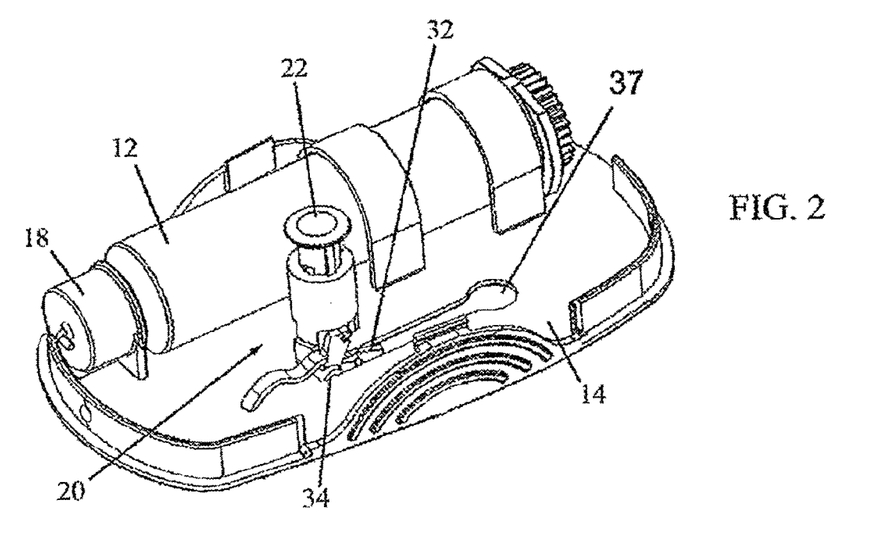

Reference is now made to FIGS. 1 and 2, which illustrate apparatus 10 for administering a substance, for example, insulin, to a subject, in accordance with an embodiment of the present invention. Typically, apparatus 10 includes a vial 12 (FIG. 2) that contains the substance to be administered to a subject. The term vial encompasses any kind of reservoir or container for storing the substance to be administered and is not limited to any size or shape.

As seen in FIG. 2, vial 12 may be mounted on a housing base 14. A housing top 16 (FIG. 1) may cover the assembly and may be secured to base 14. For some applications, a vial piercing mechanism 18 is movably (e.g., rotatably) coupled to housing base 14 and pierces the distal end of vial 12. The substance to be administered flows from vial 12 to an activation mechanism 20 via a tube (not shown). The activation mechanism 20 may have a control button 22 and is typically coupled to the housing base 14. The activation mechanism 20 is configured to insert a cannula and/or a needle through the subject's skin and to deliver the substance via the cannula and/or the needle. The embodiments of the invention are described with reference to a needle alone, but apply as well to a needle disposed in a cannula or any other delivery device. The term "needle" is used throughout the specification and claims to encompass all such delivery devices.

Apparatus 10 typically includes a motor, a battery and a control unit (all not shown). After the needle has penetrated the skin of the patient, the control unit controls operation of the motor to administer a controlled amount of the substance to the patient at a controlled rate of delivery. Of course, the needle assembly of the present invention can be used in other applications and does not have to be used with a controlled motorized delivery system.

Reference is now made to FIGS. 3-9, which illustrate operation of activation mechanism 20, constructed and operative in accordance with an embodiment of the present invention.

In a non-limiting embodiment of the invention, activation mechanism 20 includes control button 22 having a shaft 24 which is arranged to move (vertically downwards in the sense of the drawings) against a needle holder 26 (FIG. 4) which holds a needle 28. The shaft 24 and the needle holder 26 are both confined to move in a (e.g., tubular) housing 30, but there is a difference in their movements. Shaft 24 is confined to translate downwards in housing 30 with no rotation. In contrast, needle holder 26 can not only translate but can also rotate in housing 30, as will be explained more in detail below.

The movement of needle holder 26 is selectively impeded by a safety latch 32, which is pivotally mounted on housing base 14 about a pivot 34. Safety latch 32 is arranged to selectively pivot in and out of a complementary shaped groove 37 (FIG. 2) formed in housing base 14. Safety latch 32 includes a first arrestor 36 at a distal end thereof and a second arrestor 38 proximal to and spaced from the first arrestor 36. The arrestors may be shaped as lugs or other projections or any other structure suitable for arresting motion of needle holder 26 as will be explained below.

Figure 3:
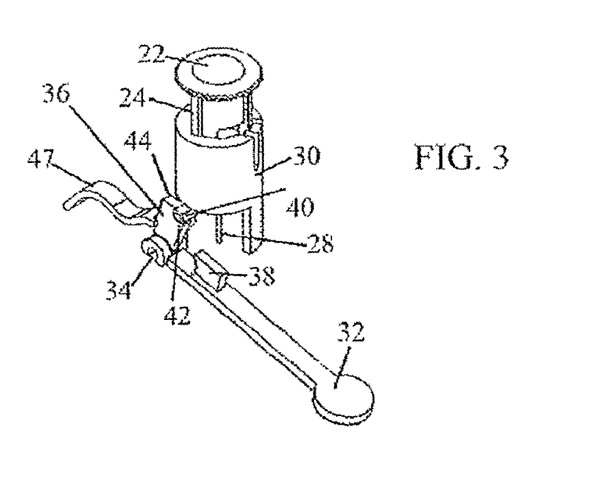
FIG. 3 is a simplified illustration of a safety latch in the down position, this being the nominal (starting) position as long as the apparatus has not yet been placed upon the user's body, and a needle holder cannot be pushed down.

FIG. 3 shows safety latch 32 in the down position, which is its nominal (starting) position as long as apparatus 10 has not yet been placed upon the user's body. In this position, first arrestor 36 abuts against an ear 40 that projects from a bottom portion of needle holder 26. It is noted that pushing ear 40 down against a surface 42 of first arrestor 36 will not cause downward movement of needle holder 26 because this will simply pivot first arrestor 36 about the pivot 34 causing another surface 44 of first arrestor 36 to abut against the bottom surface of housing 30. Thus, when safety latch 32 in the down position, needle holder cannot be pushed down (in the sense of the drawing of course).

Figure 4:
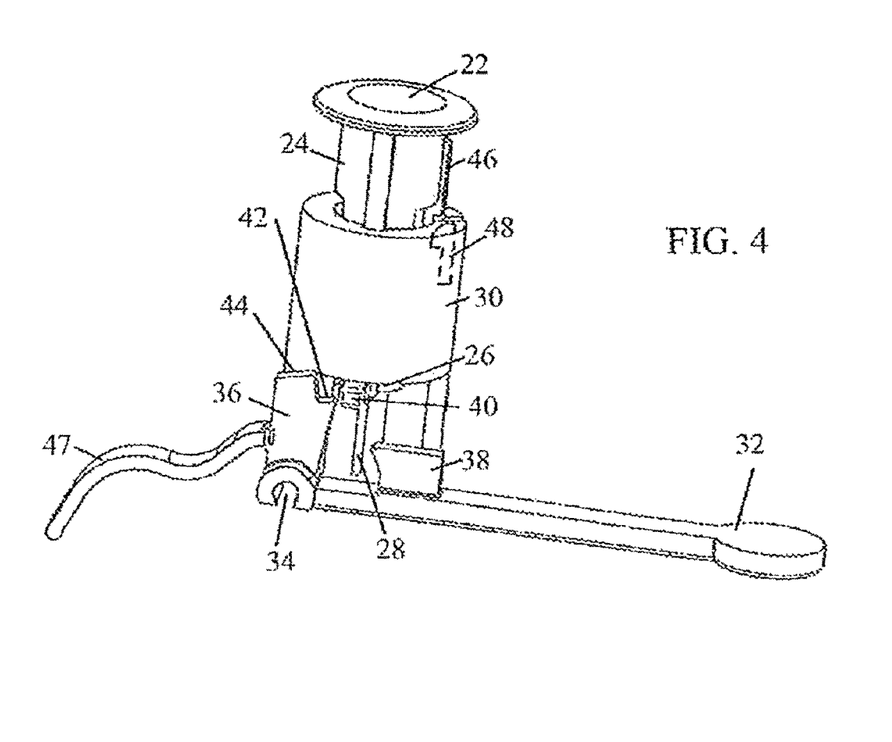
FIG. 4 is a simplified illustration of the safety latch in the up position, which is the position when the apparatus 10 has been placed upon the user's skin.

FIG. 4 shows safety latch 32 in the up position (that is, it has pivoted upwards about pivot 34), which is the position when apparatus 10 has been placed upon the user's skin. First arrestor 36 has been moved out of the way of ear 40 of needle holder 26.

Figure 5:
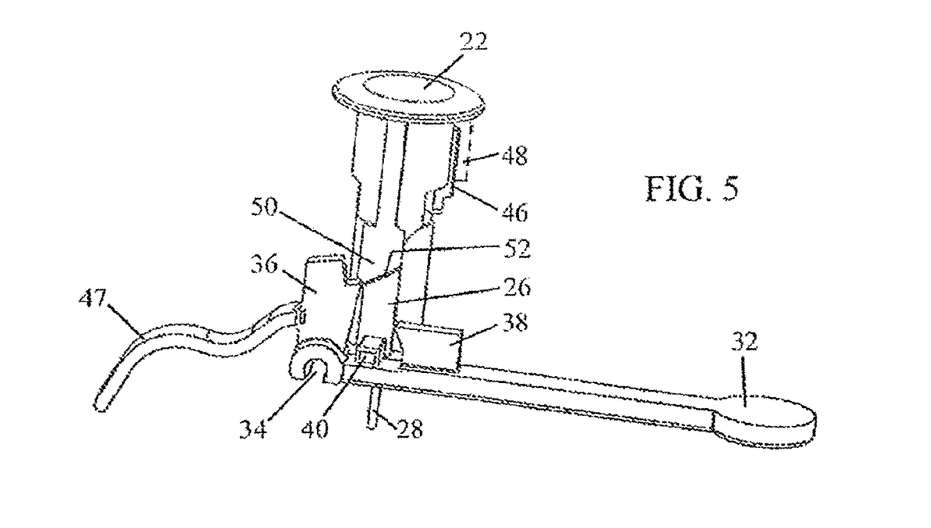
FIG. 5 is a simplified illustration of pressing the control button down which moves the needle holder downward, thereby piercing the patient's skin with the needle.

In this position, control button 22 may be pressed down to the position shown in FIG. 5. Pressing control button 22 down causes two actions. First, shaft 24 becomes locked in the down position in housing 30, such as by means of one or more splines 46, which radially project outwards from shaft 24, sliding past one or more chamfered resilient tongues 48 mounted in housing 30. After splines 46 sliding past tongues 48, splines 46 become locked in place by the action of the tongues 48 resiliently snapping back in place over them.

Second, pressing control button 22 down moves needle holder 26 downward. A slanted tongue 50 protrudes from the periphery of shaft 24 at a lower end thereof. Needle holder 26 may be cylindrical and may enter a hollow portion of shaft 24. When control button 22 is pressed down, the slanted tongue 50 rides against a slanted ramp 52 formed on needle holder 26. This action causes needle holder 26 to move down (thereby piercing the patient's skin) and to rotate counterclockwise as viewed from above control button 22.

Figure 6:
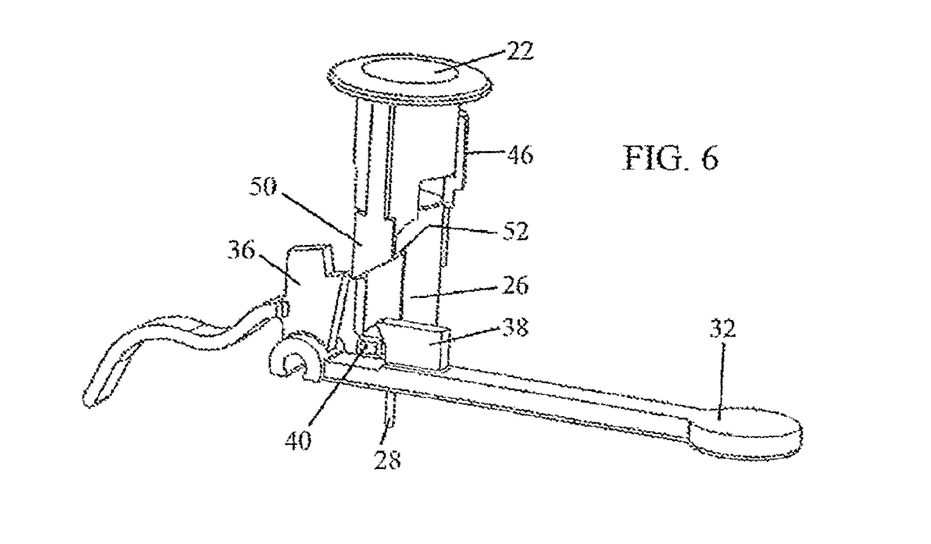
FIG. 6 is a simplified illustration of the needle holder held in place.

As seen in FIG. 6, needle holder 26 rotates sufficiently so that ear 40 is arrested by second arrestor 38. The needle 28 remains inserted in the patient for the duration of the drug administration.

It is noted that in the position of FIG. 6, slanted tongue 50 applies a downward force on ramp 52 of needle holder 26, but this force does not result in any movement of needle holder 26 on account of ear 40 being arrested by second arrestor 38.

Figure 7:
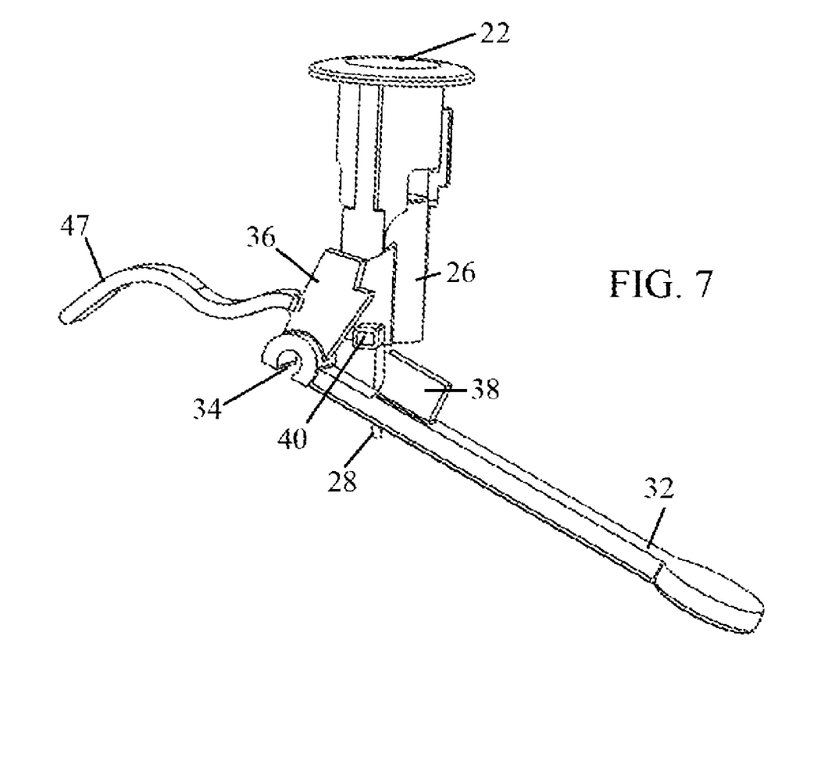
FIG. 7 is a simplified illustration of lifting the apparatus off the patient's body after finishing the drug administration, which causes the safety latch to move back to the down position.
Figure 8:
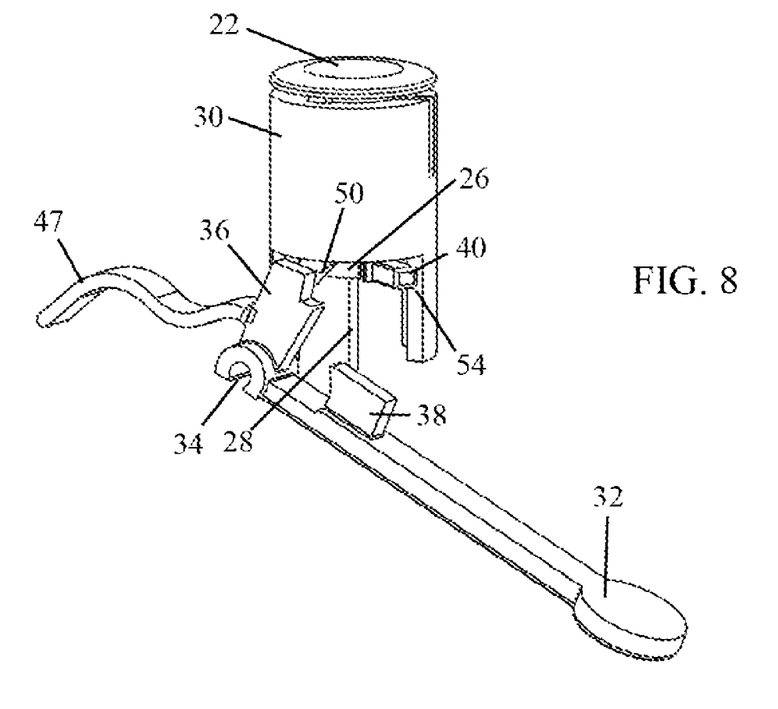
FIG. 8 is a simplified illustration of the needle holder moving back up and getting stopped in the up position with the needle retracted back into the housing of the apparatus.
Figure 9:
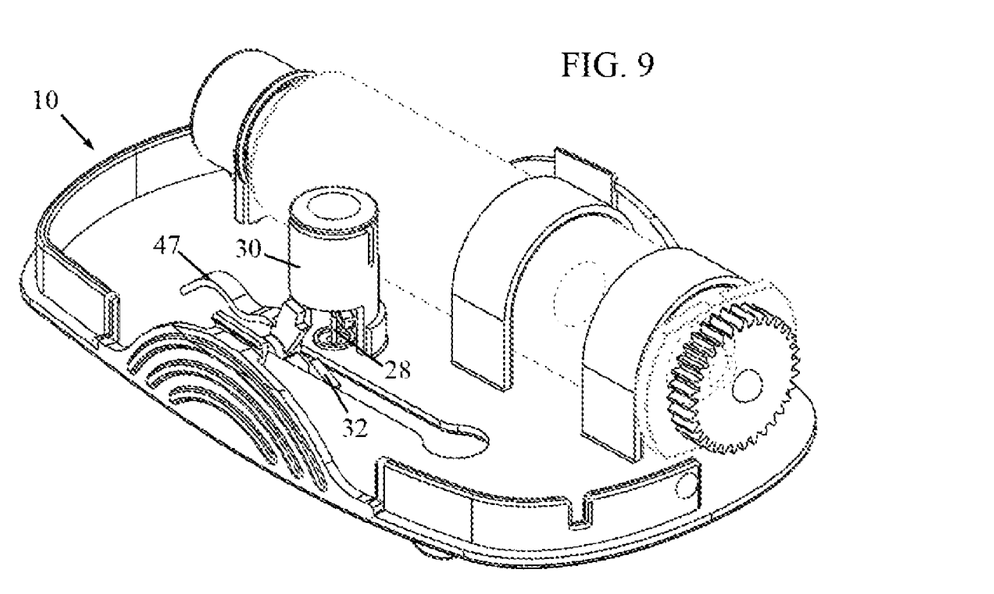
FIG. 9 is a simplified illustration of the final position of the needle trapped back inside the apparatus in a safe position.

After finishing the drug administration, apparatus 10 is lifted off the patient's body. This causes safety latch 32 to move back to the down position as shown in FIG. 7, thereby moving second arrestor 38 away from ear 40. A biasing device 47, such as a leaf spring biased between first arrestor 36 and housing base 14, may be employed to impart a returning force on safety latch 32 to move it back to the down position. Alternatively, an adhesive (not shown) may be used to stick the apparatus 10 on the patient's skin. When apparatus 10 is pulled off the skin, the adhesive resists the force to pull the device off the skin and this resistive force may impart the returning force on safety latch 32 to move it back to the down position. Since slanted tongue 50 applies a downward force on ramp 52, needle holder 26 is now free to continue rotating counterclockwise by the action of slanted tongue 50 on ramp 52. Needle holder 26 rotates counterclockwise until slanted tongue 50 slides off ramp 52. At this point, needle holder 26 jumps back up and ear 40 gets caught on a shoulder 54 formed on housing 30 as shown in FIG. 8. In this position, needle holder 26 cannot move back down because of ear 40 being arrested against shoulder 54. FIG. 9 shows the final position of the needle 28 trapped back inside apparatus 10 in a safe position. Apparatus 10 may now be safely discarded.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A needle assembly adapted for fluid communication with a vial containing a substance to be delivered to a subject, the needle assembly comprising:
    a needle held in a needle holder, said needle holder confined to move in a housing; and
    an activation mechanism for activating delivery of the substance through said needle, said activation mechanism comprising a safety latch having a down position that initially impedes movement of said needle holder, wherein when said safety latch is placed on the subject, said safety latch moves from said down position to an up position, in said up position, said needle holder is movable to cause said needle to protrude outwards of said housing to pierce the subject to allow administration of the substance to the subject.

2. The needle assembly according to claim 1, wherein said safety latch is pivotally mounted on a base about a pivot.

3. The needle assembly according to claim 2, wherein said safety latch is arranged to selectively pivot in and out of a complimentary shaped groove formed in said base.

4. The needle assembly according to claim 1, wherein said safety latch comprises a first arrestor at a distal end thereof and a second arrestor proximal to and spaced from said first arrestor, said first and second arrestors being arranged for selectively arresting motion of said needle holder.

5. The needle assembly according to claim 4, wherein said safety latch initially impedes movement of said needle holder by being in said down position wherein said first arrestor abuts against an ear that projects from a bottom portion of said needle holder, thereby arresting movement of said needle holder.

6. The needle assembly according to claim 5, wherein when said safety latch is placed on the subject, said safety latch moves to said up position such that said first arrestor moves away from said ear of said needle holder to permit movement of said needle holder.

7. The needle assembly according to claim 6, further comprising a control button that has a shaft, wherein a slanted tongue protrudes from a periphery of said shaft at a lower end thereof, and wherein when said safety latch is placed on the subject and said control button is moved, said slanted tongue applies a force against a ramp formed on said needle holder, thereby causing said needle holder to move and to rotate as said needle moves outwards of said housing.

8. The needle assembly according to claim 7, wherein said needle holder rotates sufficiently so that said ear is arrested by said second arrestor.

9. The needle assembly according to claim 7, wherein moving said safety latch off the subject causes said second arrestor to move away from said ear and causes said needle holder to continue to rotate due to said slanted tongue still applying a force on said ramp, wherein said needle holder rotates until said slanted tongue moves off said ramp, whereupon said needle holder moves so that said ear gets caught on a shoulder formed on said housing, thereby trapping said needle in said housing.

10. The needle assembly according to claim 7, wherein when said control button is moved so that said slanted tongue applies the force against said ramp, said control button becomes locked in said housing.

11. The needle assembly according to claim 1, wherein said safety latch is biased to said down position by a biasing device.

12. The needle assembly according to claim 11, wherein said biasing device is a spring.

* * * * *